United States Patent [19]
Holdredge et al.

[11] Patent Number: 5,073,825
[45] Date of Patent: * Dec. 17, 1991

[54] CONVERTIBLE VISUAL DISPLAY DEVICE

[76] Inventors: Terry K. Holdredge; Susan S. Holdredge, both of 1303 Hanover Rd., Anderson, S.C. 29621

[*] Notice: The portion of the term of this patent subsequent to Jul. 3, 2007 has been disclaimed.

[21] Appl. No.: 541,512

[22] Filed: Jun. 21, 1990

Related U.S. Application Data

[63] Continuation of Ser. No. 34,691, Apr. 6, 1987, Pat. No. 4,939,582.

[51] Int. Cl.$^5$ ............................................... H04N 5/64
[52] U.S. Cl. ........................................ 358/254; 5/113; 5/100; 358/93; 358/255; 434/307; 434/432
[58] Field of Search ................. 358/254, 255, 93, 108, 358/249; 434/307, 432; 5/512, 93 R, 113, 100, 414, 93 B; 297/184, 217; 600/21, 22; 128/897, 849

[56] References Cited

U.S. PATENT DOCUMENTS 4,779,922 10/1988 Cooper .................................. 297/174
4,939,582 7/1990 Holdredge et al. ................. 358/254

Primary Examiner—Jin F. Ng
Assistant Examiner—Jerome Grant, II
Attorney, Agent, or Firm—Cort Flint

[57] ABSTRACT

A convertible audio-visual display center adapted to reproduce visual images on a video display unit such as a television and audio reproductions of sound or music for the entertainment and/or education of infants in their cribs. The same device is readily convertible to usage as a work station for a computer console with simple adjustments.

14 Claims, 4 Drawing Sheets

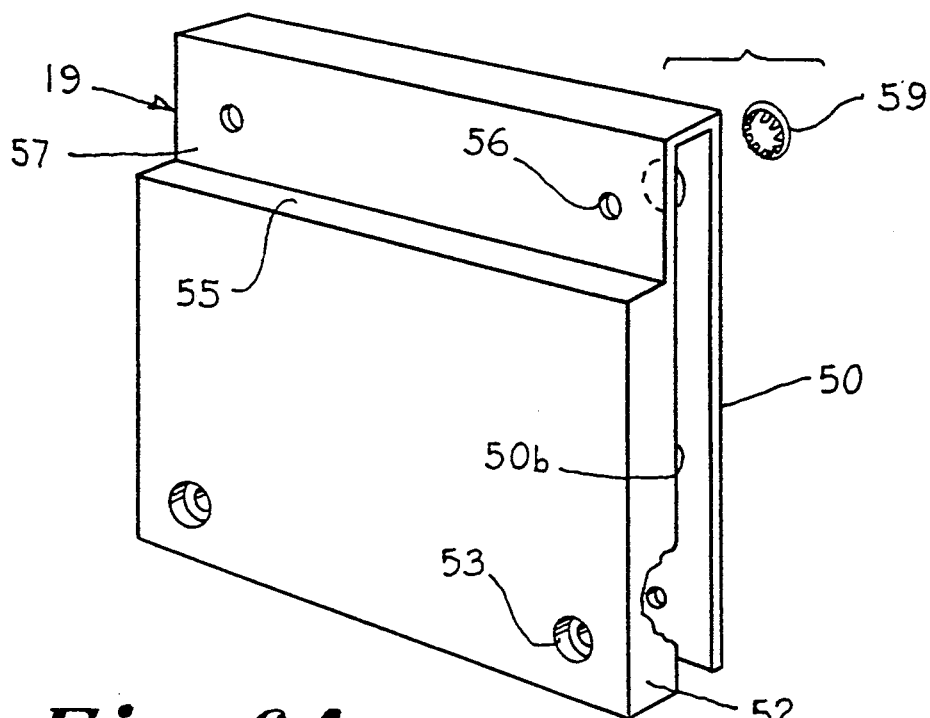
Fig. 6-A.
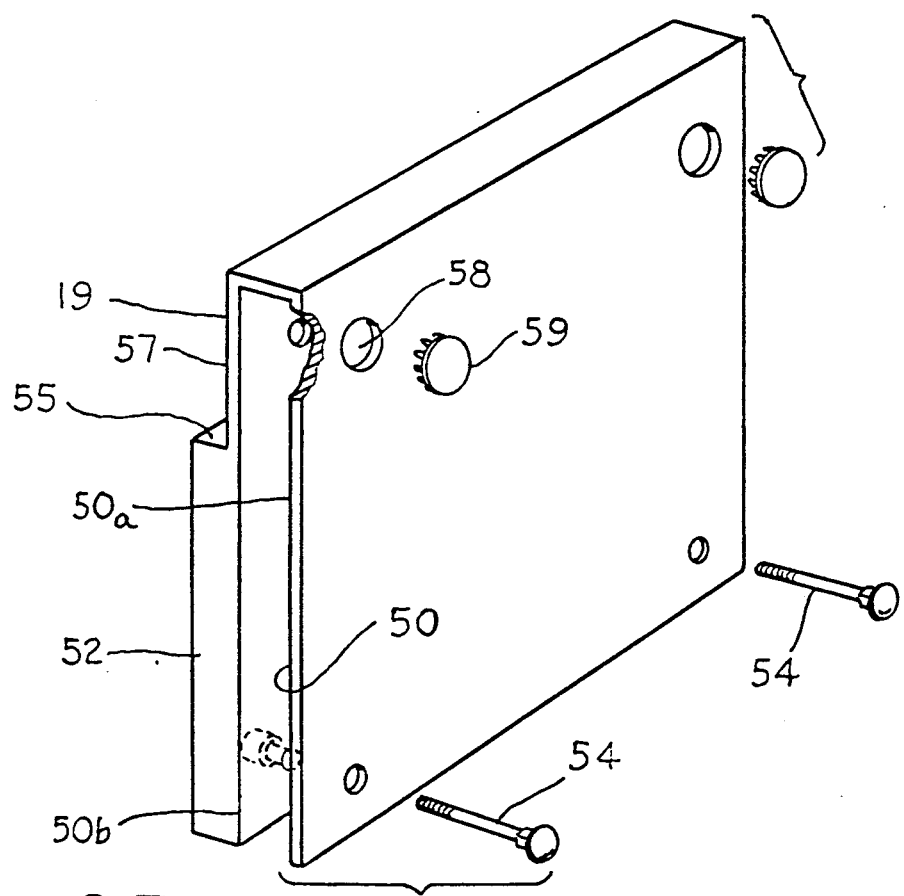
Fig. 6-B.

CONVERTIBLE VISUAL DISPLAY DEVICE

This is a continuation of copending application(s) Ser. No. 07/034,691 filed on 04-06-87 now U.S. Pat. No. 4,939,582.

BACKGROUND OF THE INVENTION

This invention relates to a convertible audio-visual display device. It is particularly related to a device which will mount on the baby's crib and provide audio and visual stimulation for the baby for entertaining and educating the baby. The unit converts to a useful, computer station by means of simple adjustments to permit the parents or others to utilize the device with a home or personal computer or word processor.

In the past, television cameras have been used to monitor infants, patients, prisoners, and the like and mothers have permitted their older children to watch television and the like to entertain them when they were older. However, nothing has been done to entertain and to stimulate younger children, for example, infants who are confined to cribs.

SUMMARY OF THE INVENTION

In the instant invention a canopy is provided which has an end wall, a top horizontal wall, and two side walls with the bottom and the front walls being open. The canopy is adapted to be securely mounted on the crib so as to provide secure means for fastening said canopy to the crib so that the canopy lies over where the baby normally rests. The top wall of the canopy (when the canopy is in place on the crib) is provided with a recess for mounting and supporting an audio-visual unit. The side walls of the canopy are adapted to receive, and to support, speaker means.

When the canopy is removed from the crib it is adapted for its end wall to rest on a table top or desk top or the like and to, in turn, support a computer or word processing console.

It is an object of the invention to provide a convertible audio-visual device which serves the multi-function of entertaining young babies either audibly or visually or in combination.

It is another object of the invention to provide an audio-visual device which can support and compliment a computer console with a single adjustment of the device.

These and other objects will become apparent when reading the attached specification in conjunction with the drawings appended thereto.

BRIEF DESCRIPTION OF THE DRAWINGS

The construction designed to carry out the invention will hereinafter be described, together with other features thereof.

The invention will be more readily understood from a reading of the following specification and, by reference to the accompanying drawings forming a part thereof, wherein an example of the invention is shown, and wherein:

FIG. 6A is a front perspective view of the adapter for supporting the canopy securely on the headboard of the crib;

FIG. 6B is a rear perspective view of the adapter for supporting the canopy securely on the headboard of the crib;

DETAILED DESCRIPTION OF THE INVENTION

Figure 1:
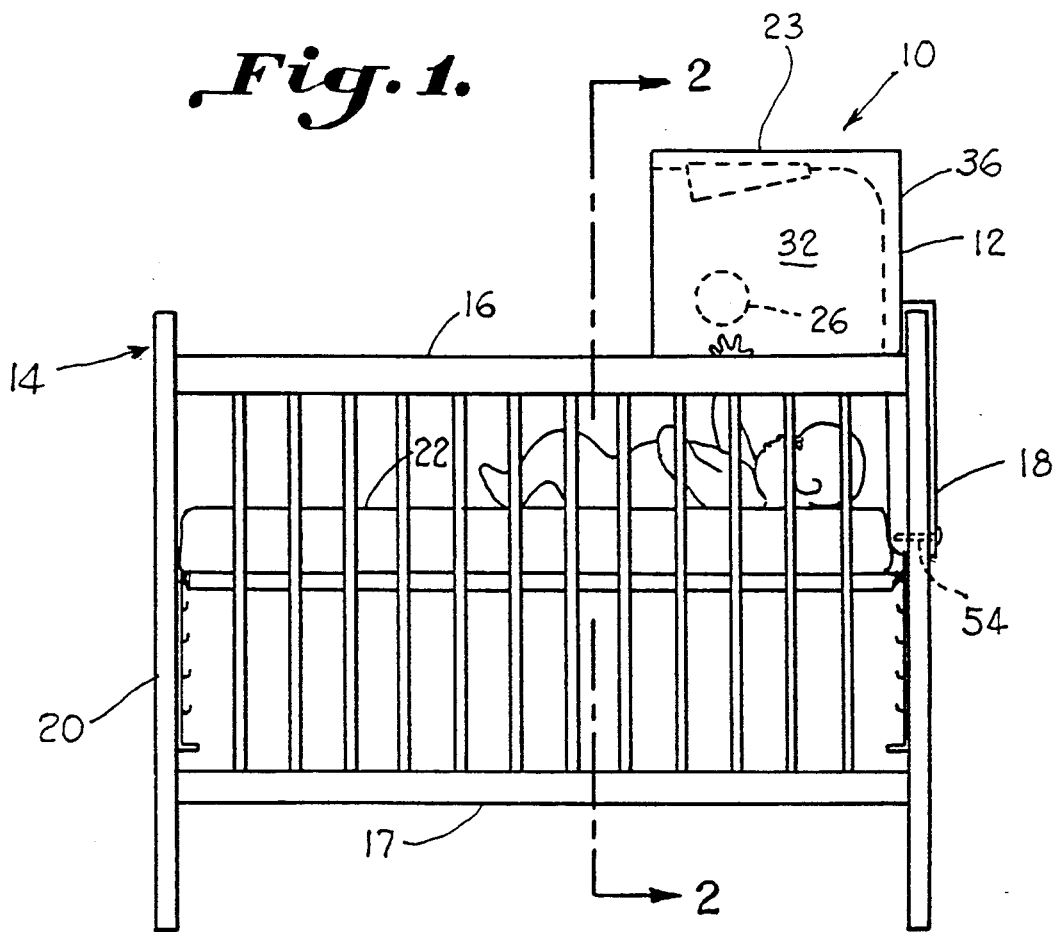
FIG. 1 is a side elevation of a crib showing the canopy of the invention in place thereon.
Figure 2:
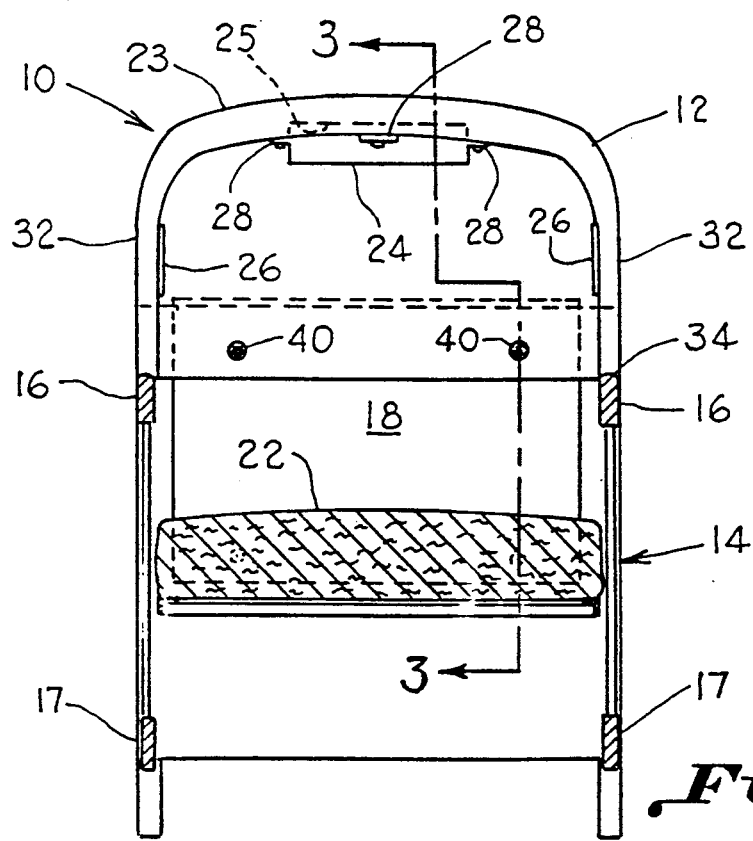
FIG. 2 is a cross-sectional view taken along lines 2—2 of FIG. 1.
Figures 3, 5:
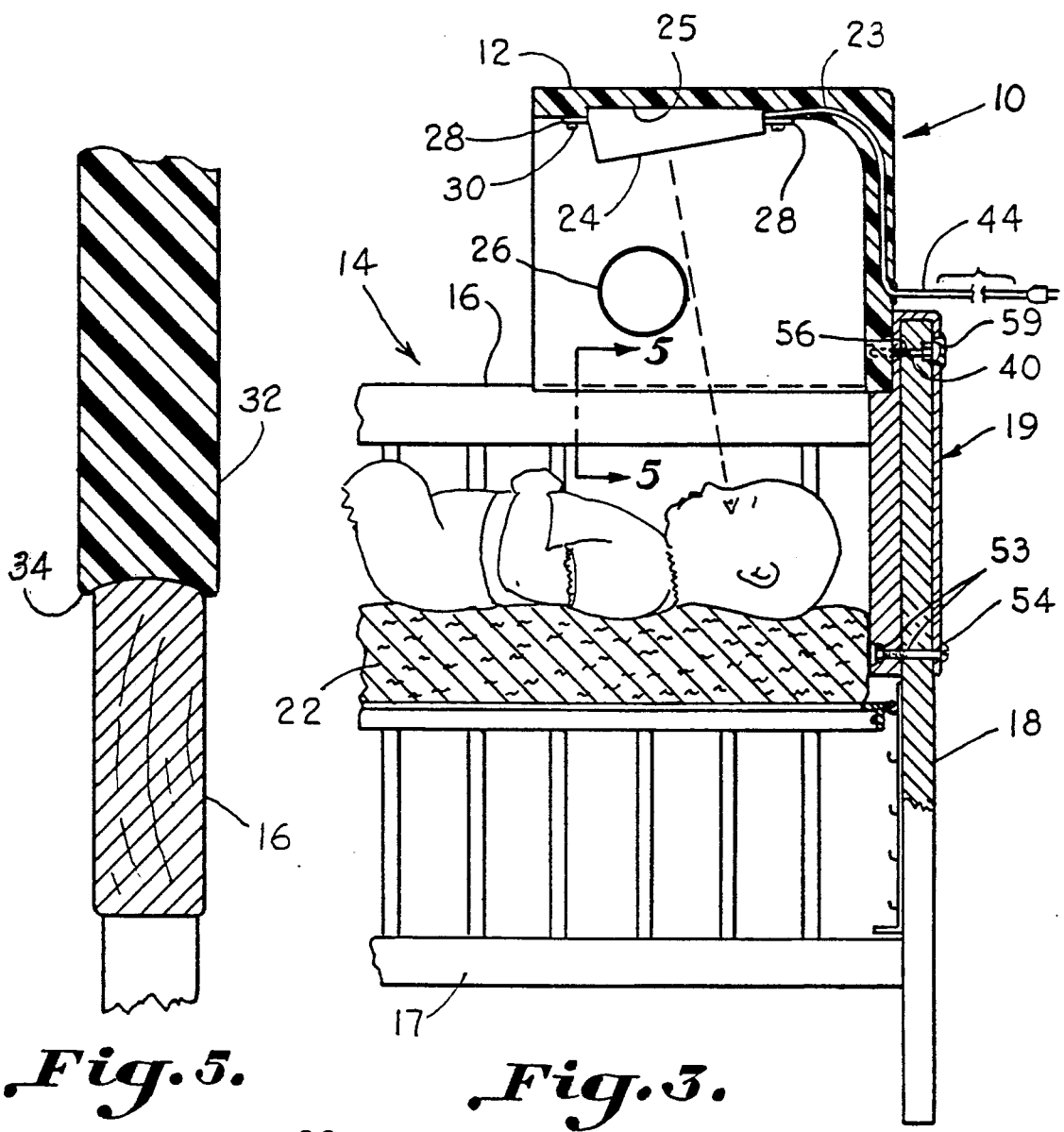
FIG. 3 is a sectional view taken along lines 3—3 of FIG. 2.
FIG. 5 is an enlarged cross-sectional view showing one of the side walls of the canopy as it fits on the top rail of a crib.
Figure 4:
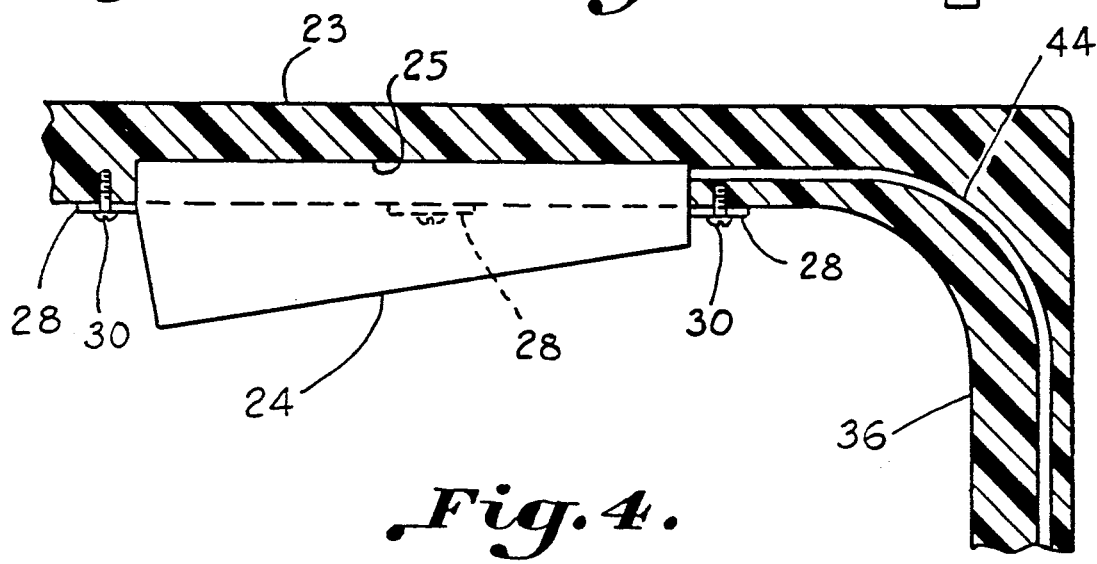
FIG. 4 is an enlarged side view of the device of the invention as seen in FIG. 3 and shows more details of the mounting of the visual display unit in the canopy.

Referring now to FIGS. 1, 2, 3, 4, 5, 6A and 6B wherein is illustrated the convertible audio-visual display center 10 which comprises a canopy 12 resting on a crib 14. Canopy 12 is supported by the top side rails 16 and on the head board 18 by an adapter 19, which will be described in detail, below. The crib also includes side and bottom rails 17, foot board 20 and a mattress 22.

Canopy 12 comprises a top wall 23, an end wall 36, and side walls 32. Top wall 23 has a recess 25 into which is fitted a video display unit 24. The video display unit 24 is held within the recess 25 by means of brackets 28 and bolts or screws 30. As can best be seen in FIGS. 3 and 4, the top of video display unit 24 is disposed in the recess adjacent to end wall 36 when the canopy is in place on the crib. Furthermore, the screen of the video display unit is tilted so that the bottom of the screen is closer to the surface of mattress 22 than is the top of the screen. The reason for this being that the baby, when lying on mattress 22 will have a more comfortable view of the screen than it would have if the screen was flush with the surface of the top wall of the canopy.

In each side wall 32 of the canopy is disposed at least one speaker 26 for conveying sounds such as voices, music, or the like for the listening pleasure of the baby. Speakers 26 and video display unit 24 are connected to a video and/or audio source by means of a coaxial cable 44 or the like. The source to which the coaxial cable 44 or the speakers are connected may be a radio, stereo, television, video cassette recorder, or the like for generating the audio and/or video signals to be reproduced by the video display unit and/or the speakers.

Whenever canopy 12 is in position bridging the side rails 16 of the crib, it is supported by the side rails and the head board 18 through adapter 19. Each canopy side wall 32 terminates in a foot 34 at the bottom edge of said side walls which is adapted to receive the top surface of top rails 16 as can best be seen in FIG. 5. In addition, canopy end wall 36 terminates in an end portion which rests upon the adapter 19 supported by the upper part of the head board 18 as best seen in FIG. 6. Canopy end wall 36 is held securely to head board 18 by means of a plurality of bolts 40 and nuts 42. Thus, when the canopy 12 is firmly attached to the crib there is no likelihood or possibility that the canopy would be dislodged or fall upon the baby.

Referring now more particularly to FIGS. 6A and 6B wherein adapter 19 is illustrated in perspective and in detail, adapter 19 has a U-shaped portion 50 having legs 50a and 50b which straddle headboard 18. On the mattress side of the headboard is a thickened portion 52 which extends between the mattress and the headboard and is held in place in contact with the headboard by means of bolts 54 which extend through openings 53 in both the headboard and the adapter. Nuts may be threaded on bolts 54 to securely hold the adapter in place against the headboard.

Near the upper end of the adapter 19 is a reduced portion 57 to form a ledge 55 which has a thickness equal to the thickness of the canopy end 36. When the canopy end is in place on the bolts 40 extend through holes 56 into the wall of the end portion and securely bolt the canopy end to adapter 19. Access openings 58 are provided in the rear wall of portion 50 of the adapter to permit bolts 40 to be threaded into the canopy. Covers 59 are provided for filling the access openings once the adapter is firmly and securely bolted to the canopy end for sake of appearance.

The adapter 19, as described herein, may be formed of a rigid plastic or from steel. In either case, the surface of thickened portion 52 will be padded where it comes, or lies, adjacent to the head of the baby, in operation, so as to avoid harmful contact between the baby and the adapter.

Figure 7:
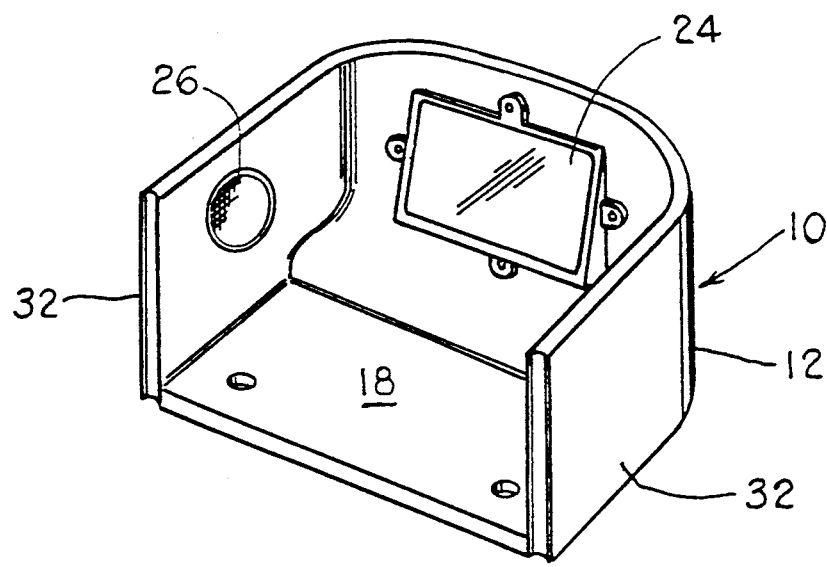
FIG. 7 is an exploded perspective view of the video display unit and a computer console with the canopy removed from the crib and supported on a table or desk.

When it is desired to convert the audio-visual display center 10 for use as a computer console or work station, the canopy 12 is disconnected from the crib and the adapter and it is placed onto a table top with the canopy end 36 in the horizontal plane and the canopy top wall 23 now in the vertical plane, as seen best in FIG. 7. When the conversion is made the video display unit 24 is loosened in its brackets 28 and bolts 30 and is reversed one hundred and eighty degrees (180°) with the top of the display unit now being adjacent to the open end of top of the canopy 12. The keyboard 46 for the computer is now supported by end wall 18, which is now in the horizontal plane, and the keyboard may be attached to end 18 by suitable brackets or screws such as brackets 28 and bolts or screws 30. In this case, the cable 44 will be connected to the keyboard of the computer as desired and the video display unit 24 will now display the results of the operation of the computer.

Figure 8:
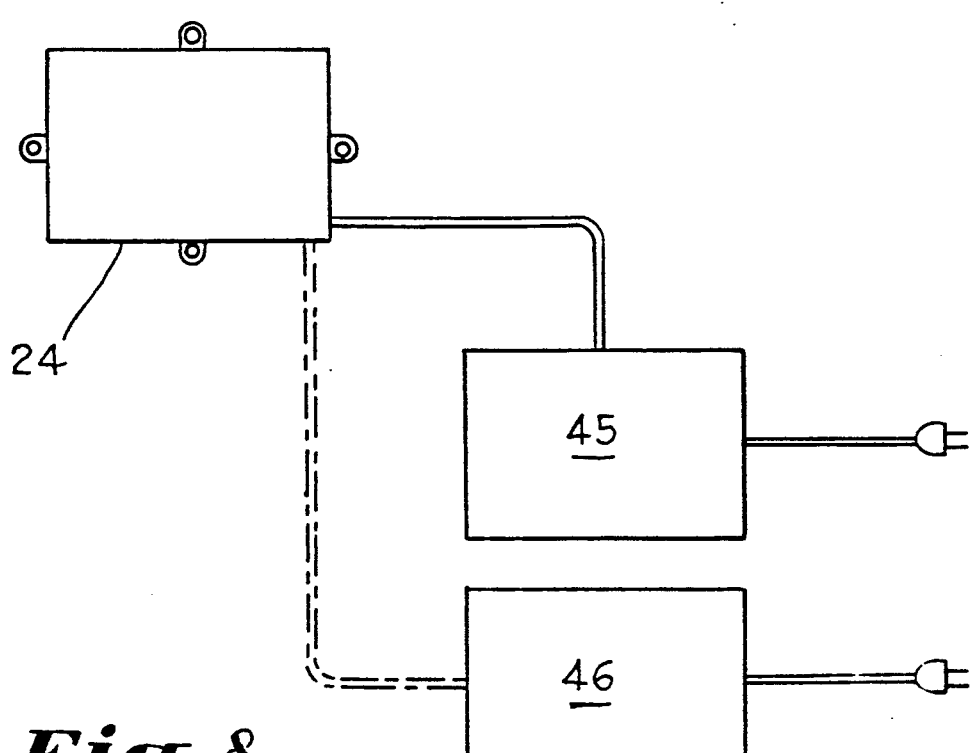
FIG. 8 is a diagramatic view showing the video display unit alternately connected to a video source or to personal computer.

As seen in FIG. 8, the video display unit 24 may be connected alternately to either the video source 45 or to a computer console 36 depending on which mode of operation is desired at the time.

The video display unit 24 disclosed herein may be any state of the art video display units available in the market place. This may use a picture tube or a liquid display, as desired, and as required by space requirements, the selection of which lies within the scope of those skilled in the video art. The particular type of video display unit is not critical to the operation of the present invention.

The words used to describe this invention herein are words of description only and are not deemed to be limiting in nature. The scope of applicant's protection is to be measured only by the claims appended hereto.

It is also understood that the means for connecting the video display unit to the canopy may vary and that the coaxial cable may be replaced by other suitable connectors for conveying the electronic signals to the video display unit.

While a preferred embodiment of the invention has been described using specific terms, such description is for illustrative purposes only, and it is to be understood that changes and variations may be made without departing from the spirit or scope of the following claims.

What is claimed is:

1. A visual display system for a bed which can be viewed by a person lying in a supine position on said bed comprising:
   a canopy disposed above and spanning said bed adjacent one end thereof;
   said canopy including a first wall means and a second wall means intersecting one another;
   a visual display unit carried by said first wall means having a display screen for viewing by said person in said supine position;
   mounting means for carrying said visual display unit in a viewing position on said first wall means with an image on said display screen being oriented in the same direction as said person lying below said canopy in said supine position; and
   support means supporting said canopy above said bed with said display screen disposed in said viewing position generally overhead of said person in said supine position.

2. The system of claim 1 wherein said canopy is convertible and said visual display unit on said first wall means has a first viewing position in which display visual images are displayed in a first plane for viewing in said supine position, and has a second viewing position in which said visual images are displayed in a second plane at an angle to said first plane for viewing in a seated position; said mounting means mounting said visual display unit on said first wall means in said first viewing position and in said second viewing position rotated from said first viewing position; and said support means supporting said canopy with said first wall means in either a substantially horizontal or a vertical position for viewing in said first and second viewing positions, respectively.

3. The system of claim 2 wherein a top of said images on said display screen are near a line of intersection of said first and second wall means in said first viewing position.

4. The system of claim 2 wherein a bottom of said images on said display screen are near a line of intersection of said first and second wall means in said second viewing position.

5. The system of claim 2 wherein said mounting means mounts said visual display unit so that a top of said visual images are closer to a plane of said first wall means in said first and second viewing positions.

6. The system of claim 2 wherein said first wall means extends in a substantially vertical plane, and said second wall means rests on a flat surface in said second viewing position.

7. The system of claim 6 wherein said second wall means provides a support for a computer keyboard.

8. The system of claim 2 wherein said mounting means mounts said visual display unit for rotation of said display screen generally 180° between said first viewing position and said second viewing position.

9. The system of claim 1 wherein said display screen is inclined relative to said first wall means in said viewing position.

10. The system of claim 2 wherein said display screen is inclined relative to said first wall means in said viewing position.

11. The system of claim 1 wherein said canopy includes side wall means, and audio means carried by said side wall means.

12. The system of claim 1 wherein said mounting means comprising a recess formed in said first wall means; and means mounting said visual display unit at least partially within said recess.

13. The system of claim 1 wherein said canopy is adapted for use with an infant's crib; and includes adapter means for securing and carrying said canopy over said crib near a headboard of said crib.

14. The system of claim 13 wherein said canopy includes first and second side walls connected to at least one of said first and second wall means of said canopy which engage top rails of said crib.

* * * * *